(12) United States Patent
Kummailil et al.

(10) Patent No.: US 12,127,780 B2
(45) Date of Patent: Oct. 29, 2024

(54) MEDICAL DEVICES AND RELATED METHODS

(71) Applicant: Boston Scientific Scimed, Inc., Maple Grove, MN (US)

(72) Inventors: John Kummailil, Sherborn, MA (US); Matthew P. Jones, Shoreview, MN (US); Sverre Gropen, Minneapolis, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 557 days.

(21) Appl. No.: 17/447,936

(22) Filed: Sep. 17, 2021

(65) Prior Publication Data

US 2022/0096141 A1   Mar. 31, 2022

Related U.S. Application Data (60) Provisional application No. 63/083,148, filed on Sep. 25, 2020.

(51) Int. Cl.
*A61B 18/14* (2006.01)
*A61B 18/00* (2006.01)
*A61B 17/00* (2006.01)

(52) U.S. Cl.
CPC .... *A61B 18/14* (2013.01); *A61B 2017/00526* (2013.01); *A61B 2018/00083* (2013.01)

(58) Field of Classification Search
CPC ............ A61B 18/14; A61B 2017/00526
See application file for complete search history.

(56) References Cited

U.S. PATENT DOCUMENTS

| | | | | |
|---|---|---|---|---|
| 4,593,691 | A * | 6/1986 | Lindstrom | A61B 18/1402 606/49 |
| 7,150,747 | B1 * | 12/2006 | McDonald | A61B 18/148 606/49 |
| 2012/0022624 | A1 * | 1/2012 | Guenther | A61L 29/126 264/257 |
| 2013/0226176 | A1 | 8/2013 | Kuehner et al. | |
| 2015/0069673 | A1 | 3/2015 | Morris | |
| 2016/0038226 | A1 | 2/2016 | Brandt et al. | |
| 2020/0093537 | A1 | 3/2020 | Fischer et al. | |

OTHER PUBLICATIONS

International Search Report and Written Opinion issued in International Application No. PCT/US2021/071495, issued Jan. 5, 2022 (11 pages).

* cited by examiner

*Primary Examiner* — Erin Snelting
(74) *Attorney, Agent, or Firm* — Bookoff McAndrews, PLLC

(57) ABSTRACT

A method of forming an energy delivery portion of a medical device includes contacting a distal portion of an electrode shaft with an insulating material, and heating the insulating material to couple the insulating material to the distal portion of the electrode shaft to form an insulation tip. The distal portion of the electrode shaft includes one or more surface contours to entrain the insulating material.

19 Claims, 5 Drawing Sheets

MEDICAL DEVICES AND RELATED METHODS

CROSS-REFERENCE TO RELATED APPLICATIONS

This patent application claims the benefit under 35 U.S.C. § 119 to U.S. Provisional Patent Application No. 63/083,148, filed on Sep. 25, 2020, the entirety of which is incorporated herein by reference.

TECHNICAL FIELD

Aspects of this disclosure generally relate to medical devices and related methods. Embodiments of the disclosure relate to medical devices and related methods for forming the medical devices such that the medical devices can treat tissue by delivering electrical energy to or into tissue and/or injecting fluid into and/or under tissue with an electrode having an insulated distal tip.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle and an energy delivery device for purposes of raising, separating, flushing, cutting, dissecting, ablating, marking, coagulating, cauterizing, or otherwise treating and/or manipulating tissue. The injection and energy delivery may be performed separately. For example, in order to deliver energy to the tissue, the user may be required to remove the injection needle from the insertion device and deliver the energy delivery device through the insertion device to the tissue being targeted, and vice versa. During the procedure, the user may alternate using the injection needle and the energy delivery device, and exchanging devices may increase the duration and risks of the medical procedure. Additionally, one or more portions of the energy delivery device may inadvertently contact or harm tissue (or an inner channel of the insertion device) when energized. Furthermore, forming an energy delivery device with one or more insulated portions may be difficult, time-consuming, expensive, etc.

The devices and methods of this disclosure may rectify one or more of the deficiencies described above or address other aspects of the art.

SUMMARY

Examples of the disclosure relate to, among other things, medical devices configured for treating tissue by delivering electrical energy to the tissue, and methods for forming the medical devices. In some examples, the medical devices may also be configured to deliver fluid into and/or under the tissue. Each of the examples disclosed herein may include one or more of the features described in connection with any of the other disclosed examples.

In one example, a method of forming an energy delivery portion of a medical device may include contacting a distal portion of an electrode shaft with an insulating material, and heating the insulating material to couple the insulating material to the distal portion of the electrode shaft to form an insulation tip. The distal portion of the electrode shaft may include one or more surface contours to entrain the insulating material.

The method may include one or more of the following features. The method may further include shaping the insulating material in a mold such that the insulation tip insulates a distal end face of the electrode shaft. The electrode shaft may include an electrode shaft lumen. The method may further include an initial step of inserting a sacrificial element into a portion of the electrode shaft lumen. The method may further include removing the sacrificial element after the heating of the insulating material and shaping of the insulating material in the mold to form an insulation tip lumen that at least partially aligns with the electrode shaft lumen.

The heating of the insulating material may precede the contacting the distal portion of the electrode shaft with the insulating material. The contacting the distal portion of the electrode shaft with the insulating material may include depositing the insulating material from a molten bath on the distal portion of the electrode shaft. The contacting the distal portion of the electrode shaft with the insulating material may include positioning a glass bead around the distal portion of the electrode shaft and positioning a non-conductive material around the glass bead. The method may further include fusing the non-conductive material to the electrode shaft by at least partially melting the glass bead.

The contacting the distal portion of the electrode shaft with the insulating material may include positioning the electrode shaft adjacent to a supply of insulating material, and rotating the electrode shaft. The heating the insulating material may include directing energy from a laser toward the electrode shaft or the insulating material.

The method may further include cooling the insulating material and the electrode shaft at a controlled rate for approximately one hour. The surface contours may include a plurality of circumferential projections or a roughened surface. The surface contours may be formed by machining. The electrode shaft may include stainless steel, and the insulating material may include a glass or a ceramic. The insulating material may include one or more filler materials. The one or more filler materials may have a thermal expansion coefficient between a thermal expansion coefficient of the glass or ceramic and a thermal expansion coefficient of a material forming the electrode shaft.

In another aspect, a method of forming an energy delivery portion of a medical device may include positioning a coupling element around a distal portion of an electrode shaft, positioning a bead of insulating material around the coupling element, and heating the coupling element to at least partially melt the coupling element to secure the bead of insulating material to the electrode shaft.

The method may include one or more of the following features. The method may further include compressing the bead of insulating material around the heated coupling element. The coupling element may be formed of glass and the bead of insulating material may be formed of ceramic.

The method may further include an initial step of sintering or depositing metallic material on an inner portion of the ceramic bead of insulating material.

In yet another aspect, a method of forming an energy delivery portion of a medical device may include positioning a sacrificial element in an electrode shaft lumen of an electrode shaft, depositing an insulating material on a distal portion of the electrode shaft, and shaping the insulating material on the distal portion of the electrode shaft to form an insulation tip on the distal portion of the electrode shaft, and removing the sacrificial element from the electrode shaft lumen and the insulating material to form an insulation tip lumen that at least partially aligns with the electrode shaft lumen. The sacrificial element may extend distally beyond a distal end of the electrode shaft. The insulating material may be heated to an at least partially molten state.

The method may include one or more of the following aspects. The insulating material may be heated by directing a laser energy source toward the distal portion of the electrode shaft or toward a supply of the insulating material. The insulating material may be deposited on the distal portion of the electrode shaft by positioning the electrode shaft adjacent to the supply of insulating material, and rotating the electrode shaft.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1A illustrates an exemplary medical device.

FIG. 2A illustrates a side view of an electrode of the medical device of FIGS. 1A and 1B.

DETAILED DESCRIPTION

Examples of the disclosure include devices and methods for one or more of: forming a portion of an electrode, facilitating and improving the efficacy, efficiency, and safety of treating and/or manipulating tissue when, for example, applying electrical energy to tissue with an electrode; delivering fluid into and/or under tissue during a medical procedure through the distal end of the electrode; and insulating a distal tip of the electrode. For example, aspects of the disclosure may provide a user (e.g., physician, medical technician, or other medical service provider) with an easy, efficient, inexpensive, etc., method of forming an electrode with one or more insulated portions, for example, an insulated distal tip. Aspects of the disclosure may provide the user with a strong and/or durable connection between the electrode and the insulation. Aspects of the disclosure may provide the user with the ability to apply electrical energy or heat to tissue using a medical device having an electrode, and to deliver fluid into and/or under tissue with the same medical device. Aspects of the disclosure may provide the user with the ability to apply electrical energy or heat and deliver fluid with a reduced likelihood of damaging tissue or contacting unintended portions of the tissue. Aspects of the disclosure may help the user penetrate a layer of tissue (e.g., a submucosal layer) to cause perforation. In these aspects, an insulated portion of the device may help maintain a separation or spacing between a cutting portion of the device and other tissue. Furthermore, aspects of the disclosure include steps to manufacture or otherwise form one or more electrodes and/or distal tips of a medical device. Some aspects of the disclosure may be used in performing an endoscopic, laparoscopic, arthroscopic, gynoscopic, thoracoscopic, cystoscopic, or other type of procedure.

Reference will now be made in detail to examples of the disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 1A:
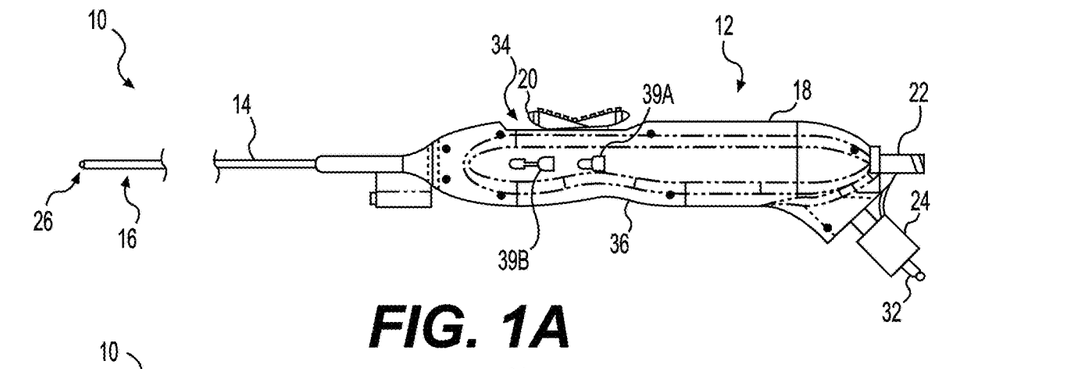
Figure 1B:
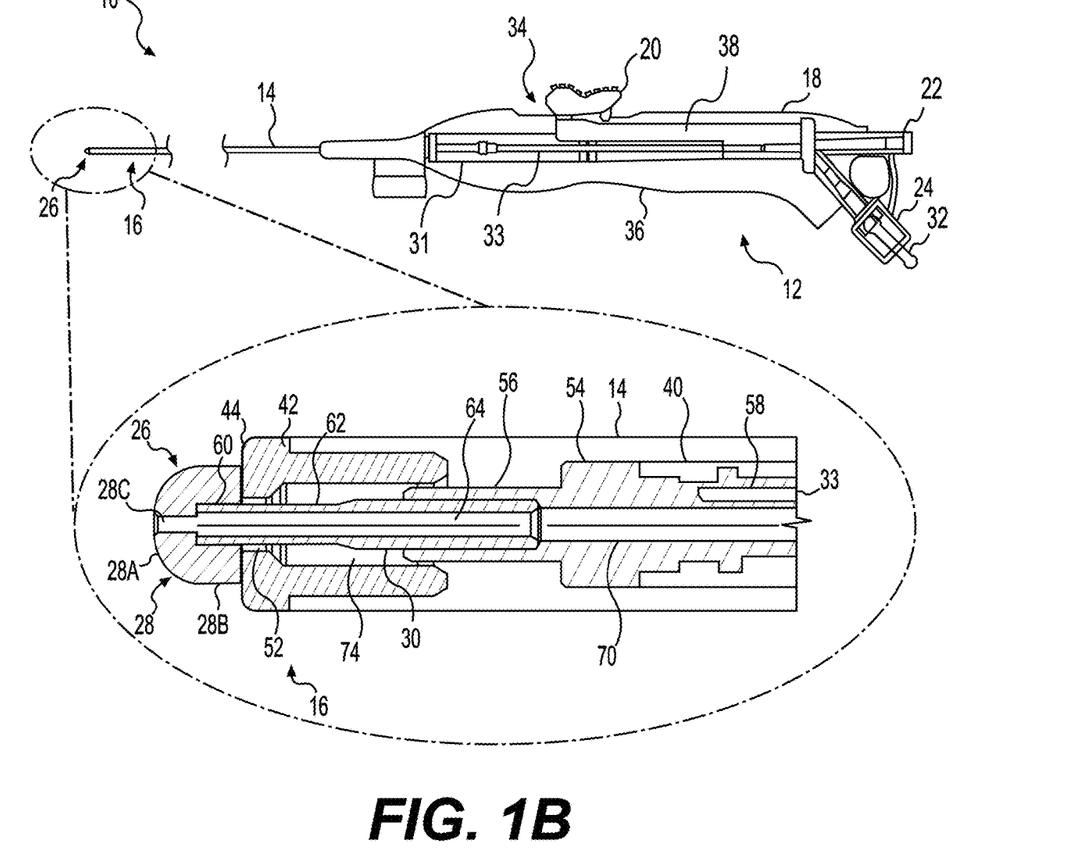
FIG. 1B illustrates a cross-sectional view of the medical device with a distal portion of the medical device enlarged, according to aspects of this disclosure.

FIGS. 1A and 1B depict a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an end effector, for example, an energy delivery portion or an electrode portion 26 (hereinafter "electrode 26"). Electrode 26 is electrically connected to hub 24, and as discussed in detail below, may include a channel fluidly connected to, or otherwise in fluid communication with, port 22. Additionally, as shown in FIG. 1B and discussed in detail below, electrode 26 may include an insulation tip 28, which may at least partially surround a distal portion of an electrode shaft 30.

Medical device 10 may be inserted into a body lumen of a subject, either through an insertion device (not shown) or alone, such that at least a portion of shaft 14 may be within the subject, while handle 12 may remain outside of the subject. Distal end 16 may be positioned at a target site within the subject. From outside of the subject, a user can manipulate handle 12. Movement of movable body 20 relative to main body 18 in a first direction (e.g., the distal direction) may extend electrode 26 relative to shaft 14 (e.g., move electrode 26 distally relative to a distal end of shaft 14). Movement of movable body 20 relative to main body 18 in a second direction (e.g., the proximal direction) may retract electrode 26 relative to shaft 14 (e.g., move electrode 26 proximally relative to a distal end of shaft 14). Although not shown, movable body 20 or additional components of handle 12 may articulate electrode 26 (or electrode 26 and distal end 16) left or right, and/or up or down relative to shaft 14.

Handle 12 may be coupled to a fluid source (not shown) via port 22. Port 22 may be in fluid communication with electrode 26 via an internal lumen 31, which may extend through handle 12 (FIG. 1B) and shaft 14. It is noted that various portions of handle 12 shown in FIG. 1B may not be to scale, in order to more fully illustrate various portions of handle 12. In one aspect, internal lumen 31 may extend longitudinally through main body 18 of handle 12 and shaft 14 to fluidly connect port 22 to electrode 26. Port 22 may be positioned on a proximal portion of main body 18, for example, a proximal end of main body 18. Alternatively, port 22 may be positioned on a distal or central portion of main body 18. Moreover, port 22 may include a one-way valve, a luer, a seal, threading, and/or any appropriate element to help maintain a secure connection between handle 12 and the fluid source, minimize or prevent back-flow (e.g., fluid flowing proximally out of port 22), and/or minimize or prevent leakage. In one example, a one-way valve may include an outer housing containing an inner elastomeric and/or gelatinous sealing member (not shown).

Handle 12 may be coupled to an energy source (not shown) via hub 24. Hub 24 may include one or more prongs or pins 32 to couple to the energy source. Hub 24 may be electrically coupled to electrode 26 via a conductive element 33, which may be electrically coupled to pin 32 and extend through handle 12 and through at least a portion of shaft 14. The energy source may be an electrocautery source, a radio frequency generator, a heating source, a current generator, etc. In one aspect, medical device 10 may be used for monopolar electrosurgery, and may include a return electrode positioned remotely from electrode 26 on or otherwise adjacent to the subject. In another aspect, medical device 10 may be used for bipolar electrosurgery. In that instance, electrode 26 may include an active electrode portion, and a return electrode may be provided at or near another portion of electrode 26 and/or shaft 14. In one example, although not shown, two conductive elements may run through shaft 14, where the conductive elements may be electrically isolated from each other, allowing one to conduct energy to the active electrode and the other to conduct energy from a return electrode.

Hub 24 may be positioned on main body 18, for example, on a proximal end of main body 18. In one aspect, port 22 may extend from the proximal end of main body 18 in a direction parallel to or coaxial with a longitudinal axis of main body 18, and hub 24 may extend from the proximal end of main body 18 at an angle transverse (e.g., approximately 45 degrees) to the longitudinal axis of main body 18. In another aspect, hub 24 may be positioned on a distal or central portion of main body 18, or on movable body 20. Although not shown, main body 18 and/or hub 24 may include a one-way valve, a luer, a seal, threading, and/or any appropriate element to help maintain a secure connection between handle 12 and the energy source, minimize or prevent back-flow (e.g., fluid flowing from port 22 and/or internal lumen 31 and proximally out of hub 24), and/or minimize or prevent leakage.

In one aspect shown in FIG. 1B, pin 32 may extend through hub 24 transverse to a longitudinal axis of handle 12, and may be electrically and physically connected to conductive element 33, such as a wire, a cable, and/or a braided sheath. Conductive element 33 may be electrically conductive or include an electrically conductive element, and conductive element 33 may extend longitudinally through internal lumen 31 and through shaft 14. As shown in FIG. 1B, fluid delivered through port 22 may surround at least a portion of conductive element 33. In one aspect, conductive element 33 may include one or more layers of insulation to help insulate conductive element 33 from the fluid in internal lumen 31. As alluded to above, a second conductive element (not shown) may be provided as a return pathway where medical device 10 has a bipolar configuration. Although not shown, in another aspect, the energy source may be a part of handle 12 (e.g., an internal battery in handle 12).

As mentioned, handle 12 may control the extension or retraction of electrode 26 relative to the distal end 16 of shaft 14. For example, main body 18 may include a slot 34, and movable body 20 may be slidably positioned within slot 34. For example, main body 18 may be configured to be held by a user's hand, and movable body 20 may be configured to be controlled by the movement of the user's thumb. For example, a side of main body 18 opposite to movable body 20 may include one or more contours 36, which may help the user grip main body 18. Movable body 20 may be lockable in one or more positions relative to main body 18, and/or may be spring-biased in a direction (e.g., toward a proximally retracted position).

Movable body 20 may be coupled to a drive element, and the drive element may impart distal or proximal movement to at least a portion of electrode 26 based on relative movement between main body 18 and movable body 20. In one aspect, conductive element 33 may also act as a drive wire, rod, cable, or the like, such that conductive element 33 may impart distal or proximal movement to at least a portion of electrode 26 while also coupling electrode 26 to hub 24, e.g., to the one or more pins 32, to deliver the energy to (and/or from) electrode 26. As shown in FIG. 1B, movable body 20 may be coupled to conductive element 33 via a coupling mechanism, for example, a coupler 38. In one aspect, coupler 38 may be physically coupled (either directly or indirectly) to movable body 20, and may also be physically coupled (either directly or indirectly) to conductive element 33 such that movement of movable body 20 extends or retracts conductive element 33, and thus extends or retracts electrode 26. It is noted that coupler 38 and/or other components within handle 12 may help maintain the electrical connection between pin 32 and conductive element 33 when conductive element 33, and thus electrode 26, is in the retracted or extended position. Alternatively, in another aspect, coupler 38 and/or other components within handle 12 may be configured to only electrically connect pin 32 and conductive element 33 when conductive element 33, and thus electrode 26, is in the extended position, or an at least partially extended position.

As shown in FIG. 1A, handle 12 may also include one or more indicators, for example, indicators 39A, 39B. For example, indicators 39A, 39B may visually indicate to the user the position of electrode 26 relative to shaft 14. The position of indicators 39A, 39B may also correspond with the position of movable body 20. For example, indicator 39A may be positioned on handle 12 at a position corresponding with a retracted position of movable body 20, and may indicate that electrode 26 is retracted relative to shaft 14. Similarly, indicator 39B may be positioned on handle 12 at a position corresponding with an extended position of movable body 20, and may indicate that electrode 26 is extended relative to shaft 14.

As shown in FIGS. 1A and 1B, shaft 14 extends from a distal portion of main body 18 to distal end 16, and may surround at least a portion of electrode 26. Shaft 14 may be a sheath that surrounds at least a portion of one or more lumens (e.g., lumen 31) and the drive wire (e.g., conductive element 33). In another aspect, shaft 14 may be an extrusion that includes one or more lumens extending from handle 12 to distal end 16.

The enlarged portion of FIG. 1B illustrates additional features of shaft 14 and distal end 16. Electrode 26 includes insulation tip 28 surrounding a distal portion of electrode shaft 30. Electrode 26 may be positioned within a portion of an end cap 42 of distal end 16. End cap 42 may include a distal end face 44. End cap 42 may be at least partially electrically insulating. For example, end cap 42 may be formed of a ceramic material or another non-conductive material. Alternatively, only distal end face 44 and an internal portion of end cap 42 that contacts and/or surrounds electrode 26 may be electrically insulating. Distal end face 44 includes a central opening 52 through which electrode 26 may extend and retract. End cap 42 includes a central portion 74 through which electrode shaft 30 may move during the extension and retraction. Additionally, although not shown, end cap 42 may be fixedly coupled to shaft 14 via welding, an adhesive, crimping, friction fit, or other appropriate coupling.

Electrode 26 may be coupled to a proximal support 54 of distal end 16, which may include a cylindrical extension 56. Proximal support 54 may be coupled to a portion of the drive wire (e.g., conductive element 33) via a drive wire receiving portion 58, for example, via welding, an adhesive, crimping, friction fit, or any other permanent or temporary coupling. Cylindrical extension 56 may extend distally and may receive at least a portion of electrode 26. Electrode 26 and cylindrical extension 56 may be coupled via welding, an adhesive, crimping, friction fit, or other appropriate coupling. In one aspect, cylindrical extension 56 may allow for different electrodes 26 to be removably coupled to distal end 16. Proximal support 54 includes a support lumen 70, and support lumen 70 fluidly connects port 22 to electrode 26, for example, via a lumen (e.g., lumen 31) through shaft 14.

Electrode 26 and proximal support 54 may be movable relative to end cap 42 in response to the relative movement of movable body 20 and main body 18 of handle 12. For example, with movable body 20 in a proximal position relative to main body 18, electrode shaft 30 may be substantially retracted within end cap 42 with only a distal portion of electrode 26 (e.g., insulation tip 28) extending distally beyond end cap 42. Then, as movable body 20 is translated distally relative to main body 18, electrode 26 and proximal support 54 translate distally relative to end cap 42 such that a greater portion of electrode 26 (e.g., electrode shaft 30) extends distally beyond end cap 42 through central opening 52.

Alternatively, although not shown, central opening 52 may be larger than insulation tip 28, and with movable body 20 in the proximal most position, electrode 26 (including insulation tip 28) may be fully retracted within central opening 52 of end cap 42. Furthermore, in one aspect, movable member 20 may have an equilibrium position relative to main body 18, and the equilibrium position may correspond to electrode shaft 30 being partially extended from end cap 42.

As shown in the enlarged portion of FIG. 1B, electrode shaft 30 includes a distal tip 60 and a longitudinal portion 62. Electrode shaft 30 may include one or more graduated portions, for example, with varying diameters, which may aid in the coupling of electrode shaft 30 to proximal support 54, may help to form one or stop surfaces (e.g., abutting an internal portion of end cap 42, etc. Electrode shaft 30 also may include an electrode shaft lumen 64 extending through electrode shaft 30, for example, extending longitudinally through a central portion of electrode shaft 30. Electrode shaft lumen 64 may be in fluid communication with port 22 via support lumen 70 through proximal support 54. In one aspect, inner sheath 40 may form at least a portion of the fluid connection between lumen 70 and port 22. Additionally, electrode shaft lumen 64 may be in fluid communication with an insulation tip lumen 28C to form a channel to deliver fluid from a distal end of electrode 26. Nevertheless, it is noted that, in some aspects, medical device 10 may be used only to deliver energy, and not to deliver fluid. In this aspect, electrode shaft 30 may not include electrode shaft lumen 64, and/or insulation tip 28 may not include insulation tip lumen 28C.

As shown in FIG. 1B, insulation tip 28 may include a distal end 28A and a side portion 28B. Distal end 28A may be rounded, for example, substantially hemispherical, and side portion 28B may include straight sides, for example, may be substantially cylindrical. In one aspect, the shapes of distal end 28A and side portion 28B may help distal end 16 be atraumatic, and/or may help abut, position, manipulate, or otherwise treat tissue, while electrode 30 may be used to cut, dissect, ablate, mark, coagulate, cauterize, or otherwise treat tissue. Nevertheless, this disclosure is not so limited, and insulation tip 28, including distal end 28A and side portion 28B, may include other shapes. For example, insulation tip 28 may be frustoconical, tapered, chamfered, filleted, beveled, or combinations thereof. In one aspect, insulation tip 28 completely surrounds or covers a distal portion (e.g., distal tip 60) of electrode shaft 30. In this aspect, insulation tip 28 may provide an insulation from the distal portion of electrode shaft 30 and at least a portion of the tissue near insulation tip 28. For example, insulation tip 28 may abut tissue, and electrode shaft 30 may be energized while insulation tip 28 helps to insulate the tissue that insulation tip 28 abuts against. Moreover, insulation tip 28 may receive distal tip 60 within approximately one half of insulation tip 28 along the longitudinal axis, which may help securely couple insulation tip 28 and electrode 30. Additionally, approximately one half of insulation tip 28 may extend distally beyond distal tip 60, which may help insulate tissue abutting distal portion 28A of insulation tip 28 when electrode 30 is energized. In some aspects, insulation tip 28 may include a thickness of approximately 1 mm to 5 mm. Furthermore, a thickness of insulation tip 28 may depend on a dielectric strength and/or other characteristics of the insulating material(s) forming insulation tip 28, the amount of energy to be delivered via electrode shaft 30, a surface roughness of electrode shaft 30, and/or one or more other characteristics of the system or treatment procedure.

As discussed below, insulation tip 28 and electrode shaft 30 may be physically coupled, for example, via one or more fusing or coupling mechanisms or techniques. Moreover, in some aspects, insulation tip 28 and electrode shaft 30 form a fluid channel that extends through both electrode shaft 30 and insulation tip 28 in order to deliver (e.g., inject) fluid to a target site (e.g., within or between layers of tissue to raise, separate, flush, or otherwise treat tissue). Electrode shaft 30 may be energized, and the exposed portion of electrode shaft 30 (e.g., longitudinal portion 62) may be used to cut, dissect, ablate, mark, coagulate, cauterize, or otherwise treat tissue. Insulation tip 28 may insulate a portion of electrode shaft 30 (e.g., distal tip 60), and may help provide a separation between the active portion of electrode shaft 30 and tissue.

Figure 2A:
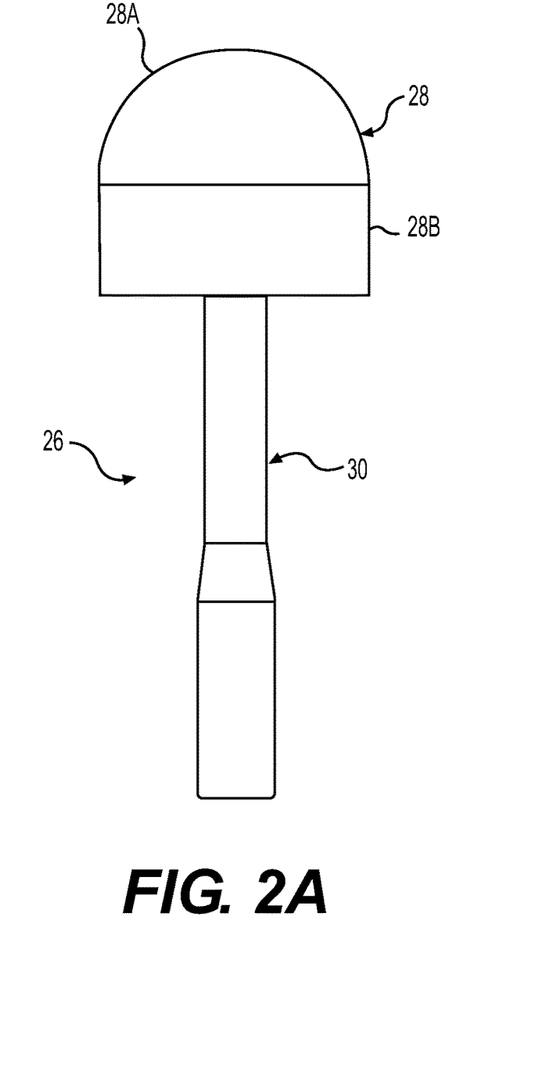
Figure 2B:
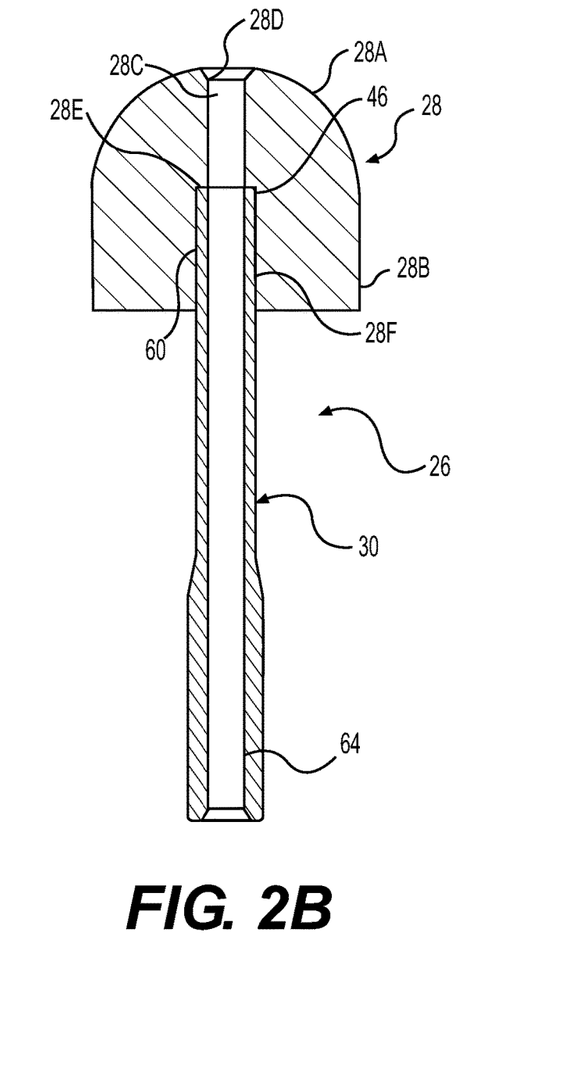
FIG. 2B illustrates a cross-sectional view of the electrode portion of FIG. 2A, according to aspects of the disclosure.

FIGS. 2A and 2B illustrate additional aspects of electrode 26 that may form a portion of distal end 16 of medical device 10. FIG. 2A shows a side view of electrode 26, and FIG. 2B shows a cross-sectional view of electrode 26. As mentioned, electrode 26 includes insulation tip 28 surrounding electrode shaft 30. Insulation tip 28 may include distal portion 28A and side portion 28B. As shown in FIGS. 1B and 2B, insulation tip 28 may include insulation tip lumen 28C. In this aspect, fluid delivered through electrode shaft lumen 64 may be delivered distally through insulation tip lumen 28C. In one aspect, electrode shaft lumen 64 and insulation tip lumen 28C may be approximately the same size. In another aspect, electrode shaft lumen 64 and insulation tip lumen 28C may be tapered distally such that distal portions of the lumens are narrower than proximal portions of the lumens. Alternatively, electrode shaft lumen 64 and insulation tip lumen 28C may be tapered proximally such that proximal portions of the lumens are narrower than distal portions of the lumens. In these aspects, varying sizes of electrode shaft lumen 64 and insulation tip lumen 28C may help increase or decrease the pressure of the fluid being delivered through the fluid channel. A distal end portion 28D of insulation tip lumen 28C may include a chamfer or angled portion, which may help disperse, direct, or otherwise control delivery of fluid to a target site. In some aspects, a chamfer or angled portion may decrease the likelihood of damaging tissue. Nevertheless, as mentioned above, in some aspects, medical device 10 may not deliver fluid, and electrode 26 may not include electrode shaft lumen 64 and/or insulation tip 28 may not include insulation tip lumen 28C.

Additionally, distal end 28A of insulation tip 28 may include an internal face 28E. When insulation tip 28 and electrode shaft 30 are coupled together, a distal end face 46 of electrode 26 may abut internal face 28E. In this aspect, insulation tip 28 may insulate distal end face 46 of electrode shaft 30.

Insulation tip 28 may be formed of one or more of a ceramic (e.g., zirconia, an alloy containing zirconium (e.g., $ZrO_2$), aluminum oxide ($Al_2O_3$), a ceramic alloy, etc.), a glass (e.g., silicon dioxide (i.e., $SiO_2$), a borosilicate glass, a silicate, etc.), a polymer material (e.g., a fluoropolymer, polyether ether ketone (PEEK), etc.), or another medically-safe, heat-resistant, and non-conductive material. Electrode shaft 30 may be formed of a conductive material, for example, a stainless steel (e.g., 316L stainless steel), titanium, or another medically-safe and conductive material. In one aspect, electrode shaft 30 may include a surface finish, for example, may be passivated per ASTM A967 Nitric 2.

Various portions of insulation tip 28 may include heights and widths, for example, as measured relative to a longitudinal axis of insulation tip 28. Insulation tip 28 may include a width (e.g., at a proximal end of side portion 28B) of approximately 2.0 to 3.0 mm, for example, approximately 2.2 mm. Insulation tip 28 may have a height (e.g., from the proximal end of side portion 28B to a distal end face of distal end 28A) of approximately 2.0 to 3.0 mm, for example, approximately 2.1 mm. For example, distal end 28A of insulation tip 28 may be rounded (e.g., substantially hemispherical), and may include a radius of approximately 0.5 to 2.0 mm, for example, approximately 1.1 mm. Although not shown, insulation tip 28 may include a cylindrical tip portion or another shape. Side portion 28B may have a height of approximately 0.5 to 1.0 mm, for example, approximately 0.9 mm. Moreover, in some aspects, the heights and widths of insulation tip 28 may vary depending on the material, size, type, intended treatment, etc. of electrode 26 and/or the material from which insulation tip 28 is formed. For example, if electrode 26 is delivering a higher energy level, insulation tip 28 may be thicker (e.g., have a larger width or height). Alternatively, if electrode 26 is delivering a lower energy lever, insulation tip 28 may be thinner (e.g., have a smaller width or height).

Additionally, as shown in FIG. 2B, the wider portion of insulation tip lumen 28C formed by radial internal portion 28F (e.g., where insulation tip 28 overlaps with electrode shaft 30) may include a height of approximately 0.5 to 1.5 mm, for example, approximately 1.0 mm, and the narrower portion of insulation tip lumen 28C (e.g., wherein insulation tip 28 does not overlap with electrode shaft 30) may include a height of approximately 0.5 to 1.5 mm, for example, approximately 1.0 mm. The wider portion of insulation tip lumen 28C formed by radial internal portion 28F (e.g., where insulation tip 28 overlaps with electrode shaft 30) may include a width of approximately 0.3 to 0.7 mm, for example, approximately 0.5 mm, and the narrower portion of insulation tip lumen 28C (e.g., wherein insulation tip 28 does not overlap with electrode shaft 30) may include a width of approximately 0.2 to 0.5 mm, for example, approximately 0.3 mm. As mentioned, distal end portion 28D may include a chamfer or angled portion, which may transition from the width of the narrowed lumen, for example, approximately 0.3 mm, to a wider width, for example, approximately 0.37 mm. In this aspect, the chamfer or angled portion of distal portion 28D may include an angle of approximately 60 degrees relative to the longitudinal axis.

Various portions of electrode shaft 30 may include heights and widths, for example, as measured relative to a longitudinal axis of electrode shaft 30. Electrode shaft 30 may include a total height of approximately 4.0 to 6.0 mm, for example, approximately 5.2 mm. In one aspect, electrode shaft lumen 64 and insulation tip lumen 28C may be approximately the same width (e.g., in a direction transverse to the longitudinal axis of electrode shaft lumen 64 and insulation tip lumen 28C). For example, electrode shaft lumen 64 and insulation tip lumen 28C may include constant widths of approximately 0.3 mm.

FIGS. 3A-3D illustrate steps of an exemplary method that may be performed to form an electrode 126 similar to electrode 26, with similar elements shown by 100 added to the reference numbers. For example, electrode 126 includes an insulation tip 128 on an electrode shaft 130. As shown in FIGS. 3A-3D, insulation tip 128 is formed by depositing molten insulating material, for example, from a molten bath on a distal portion of electrode shaft 130. The steps shown in FIGS. 3A-3D may include controlled cooling, molding, or other shaping techniques.

Figures 3A, 3B, 3C, 3D:
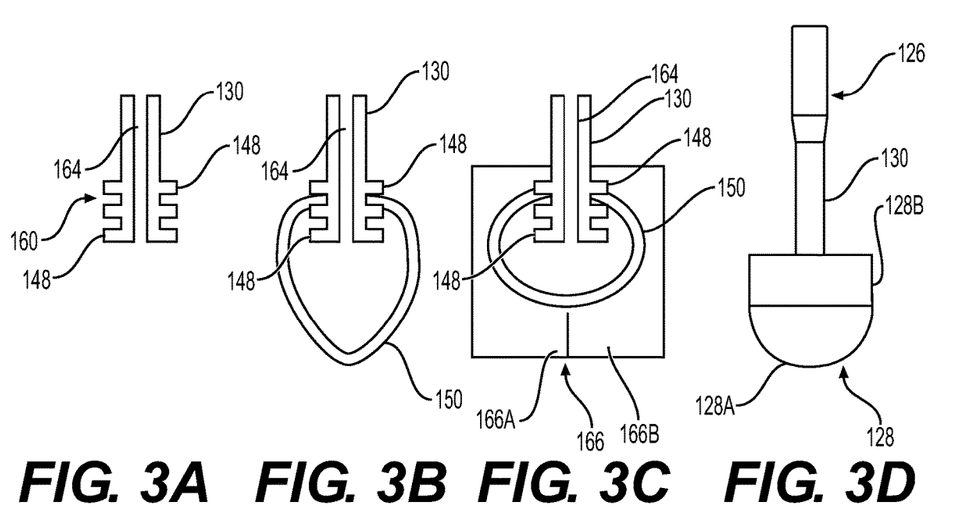
FIGS. 3A-3D illustrate views of a portion of another electrode of the medical device of FIGS. 1A and 1B in various stages of formation, according to aspects of the disclosure.

FIGS. 3A-3D illustrate a distal portion of electrode 126. As shown, a distal portion of electrode shaft 130, for example, distal tip 160, includes one or more entrainment features or surface contours 148. For example, FIGS. 3A-3C illustrate cross-sectional views of electrode 126, and surface contours 148 may be radial projections that extend away from distal tip 160 of electrode shaft 130, for example, in a direction radially outward from the longitudinal axis of electrode 126. Surface contours 148 may circumferentially surround portions of distal tip 160. Alternatively, surface contours 148 may be formed by radial projections that extend from, but do not circumferentially surround, portions of distal tip 160. Surface contours may be formed during the molding of electrode shaft 130. Alternatively, surface contours 148 may be formed by machining one or more portions of distal tip 160 or by affixing one or more surface contours 148 to distal tip 160, e.g., via welding. In another aspect, surface contours 148 may be formed by a ribbed or roughened surface on one or more portions of distal tip 160. In this aspect, a first step of forming electrode 126 includes forming electrode shaft 130 with one or more surface contours 148 on distal tip 160.

As shown in FIG. 3B, a second step of forming electrode 126 includes depositing an insulating material 150 on the distal portion of electrode shaft 130, for example, in a molten state. In one aspect, a drop, blob, or other amount of molten insulating material 150 may be applied to a distal portion of electrode shaft 130. In another aspect, the distal portion of electrode shaft 130 may be inserted into a bath of molten insulating material 150. In these aspects, surface contours 148 may help to capture, bind to, or otherwise entrain or retain insulating material 150 around electrode shaft 130. Insulating material 150 may surround the entirety of distal tip 160, or, as shown in FIG. 3B, insulating material 150 may only surround a portion of distal tip 160. For example, if surface contours 148 are formed by one or more projections, one or more of the projections may not be covered by insulating material 150. In this aspect, the uncovered surface contours 148 may provide one or more conductive projections that may be used to treat tissue.

As shown in FIG. 3C, a third step of forming electrode 126 includes shaping insulating material 150. For example, shaping insulating material 150 may include a mold 166 or other shaping mechanism. As shown in FIG. 3C, mold 166 may include two or more separate components, a first mold portion 166A and a second mold portion 166B, for example, to form a clamshell mold. In this aspect, first mold portion 166A and second mold portion 166B may be positioned around insulating material 150 and electrode shaft 130, and bringing first mold portion 166A and second mold portion 166B into abutting contact (or close to abutting contact) may squeeze or otherwise shape insulating material 150.

It is noted that the third step of forming electrode 126, shown in FIG. 3C, may be performed while insulating material 150 is still at least partially molten, for example, while insulating material 150 is malleable and has not yet fully cooled. Insulating material 150 may then cool or at least partially cool, for example, to room temperature, while surrounded by mold 166. Although not shown, electrode 126, with insulating material 150 in mold 166, may be positioned in a controlled temperature environment, for example, in order to control the cooling rate. In this aspect, a gradual cooling (e.g., over the course of approximately 1 hour) may help to couple insulating material 150 to electrode shaft 130, for example, by preventing or reducing thermal stresses caused by different cooling rates or other thermal properties of the materials, which may help to prevent breakage (e.g., cracks, uncoupling, etc.) of assembled electrode 126. Additionally, gradual cooling may help to prevent breakage of electrode 126 during usage, for example, as portions of electrode 126 heat up during energy delivery.

As mentioned, electrode shaft 130 may be formed of stainless steel. Insulating material 150 may be formed of, for example, ceramic (e.g., zirconia, an alloy containing zirconium (e.g., $ZrO_2$), aluminum oxide ($Al_2O_3$), a ceramic alloy, etc.) or other suitable materials. Alternatively or additionally, insulating material 150 may be formed of a polymer material (e.g., a fluoropolymer, polyether ether ketone (PEEK), etc.) or another biocompatible, heat-resistant, and non-conductive material, such as, for example, a glass (silicone-based, boron-based, etc.). These materials have different thermal properties, so gradual cooling may help to minimize affects these different thermal properties may have on performance, for example, the strength and/or durability of the coupling insulating material 150 to electrode shaft 130.

Lastly, once insulating material 150 has sufficiently cooled, mold 166 may be removed, forming electrode 126. For example, as shown in FIG. 3D, electrode 126 includes insulation tip 128 formed of insulating material 150 on a distal portion of electrode shaft 130. Moreover, different molds 166 may be used to shape insulating material 150 in different shapes, for example, in order to form different electrodes 126. As shown in FIG. 3D, insulation tip 128 may include a rounded distal end 128A and cylindrical side portion 128B. Additionally, insulation tip 128 may not include an insulation tip lumen. In this aspect, as shown in FIGS. 3B and 3C, insulating material 150 may surround and/or fill a distal portion of an electrode shaft lumen 164.

Figures 4A, 4B, 4C, 4D:
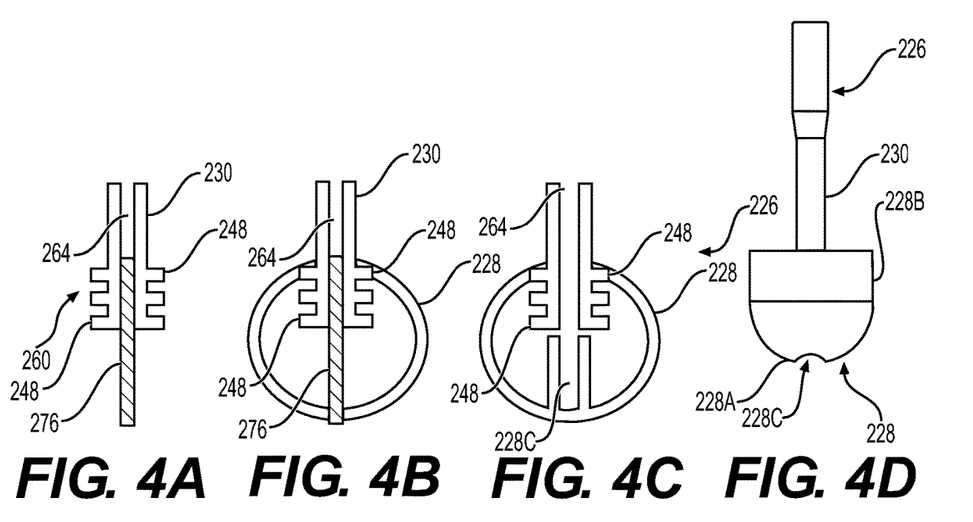
FIGS. 4A-4D illustrate views of a portion of an alternative exemplary electrode of the medical device of FIGS. 1A and 1B in various stages of formation, according to aspects of the disclosure.

FIGS. 4A-4D illustrate steps of an exemplary method that may be performed to form an electrode 226 similar to electrode 26, with similar elements shown by 200 added to the reference numbers. For example, electrode 226 includes an insulation tip 228 on an electrode shaft 230, with insulation tip 228 including a rounded distal end 228A and a cylindrical side portion 228B. Similar to FIGS. 3A-3D, insulation tip 228 may be formed by depositing insulating material from a molten bath, for example, with controlled cooling, molding, or other shaping techniques. As shown in FIG. 4D, insulation tip 228 may include an insulation tip lumen 228C, for example, fluidly connected to an electrode shaft lumen 264. Insulation tip lumen 228C may connect to a distal end of insulation tip 228 via a divot or inset portion of insulation tip 228, for example, at least partially formed by a sacrificial element 276, as discussed below. In one example, additional processing steps may be performed on insulation tip 228 (e.g., selective heating) to help shape insulation tip 228.

As shown in FIG. 4A, electrode shaft 230 includes electrode shaft lumen 264. Additionally, electrode shaft 230 may include one or more surface contours 248, for example, on a distal tip 260. Moreover, one or more frangible or sacrificial elements 276 may be positioned in a portion of electrode shaft lumen 264. Sacrificial element 276 may be a substantially rod-shaped plug. Sacrificial element 276 may extend proximally into a portion of electrode shaft lumen 264, and may extend distally of electrode shaft 230. Sacrificial element 276 may include a diameter approximately equal to an inner diameter of electrode shaft lumen 264. In one aspect, if insulating material 250 is deposited to extend approximately 5 mm beyond a distal end of electrode shaft 230, sacrificial element 276 may be approximately 20 mm long in order to extend into electrode shaft lumen 264 and also extend distally beyond electrode shaft 230. Sacrificial element 276 may be formed of one or more of graphite, boron nitride, or another appropriate (e.g., frangible) material to be removably received within electrode shaft lumen 264 and to at least partially prevent ingress of insulating material 250 into electrode shaft lumen 264 during formation of insulating material 250 on electrode 226.

As shown in FIG. 4B, insulating material 250 may be deposited on electrode shaft 230, as discussed above with respect to FIGS. 3A-3D. Surface contours 248 may help to couple insulating material 250 to electrode shaft 230. In this aspect, internal portions of insulation tip 228 may be entrained by surface contours 248 and/or may form shapes that correspond to the shape of surface contours 248 (i.e., mirror or form inverse shapes). Sacrificial element 276 may help to prevent insulating material 250 from surrounding, filling, or otherwise obstructing electrode shaft lumen 264. As discussed above, although not shown, insulating material 250 may be shaped, molded, etc., for example, via a clamshell mold, in order to form insulation tip 228. For example, the mold may include an opening to receive a portion of sacrificial element 276. Additionally, insulating material 250 and electrode shaft 230 may be gradually cooled.

As shown in FIGS. 4C and 4D, sacrificial element 276 may be removed. In one aspect, sacrificial element 276 may be removed from electrode shaft lumen 264 and insulating material 250 when insulating material 250 has partially (but not fully) cooled. With sacrificial element 276 removed, electrode shaft lumen 264 may be fluidly connected to insulation tip lumen 228C. Insulation tip lumen 228C may at least partially align with electrode shaft lumen 264. Accordingly, fluid may be delivered through electrode shaft 230 and insulation tip 228 to treat tissue, as discussed above.

Although not shown, additional processing steps may be performed, for example, to smooth out portions of insulation tip 228. For example, the removal of sacrificial element 276 may cause one or more portions of distal end 228A to include sharp edges, cracks, etc. In this aspect, one or more portions of distal end 228A may be heated (e.g., to partially melt insulating material 250) or otherwise treated to smooth out sharp edges, fill in cracks, or otherwise address inconsistent features of insulation tip 228

Figure 5:
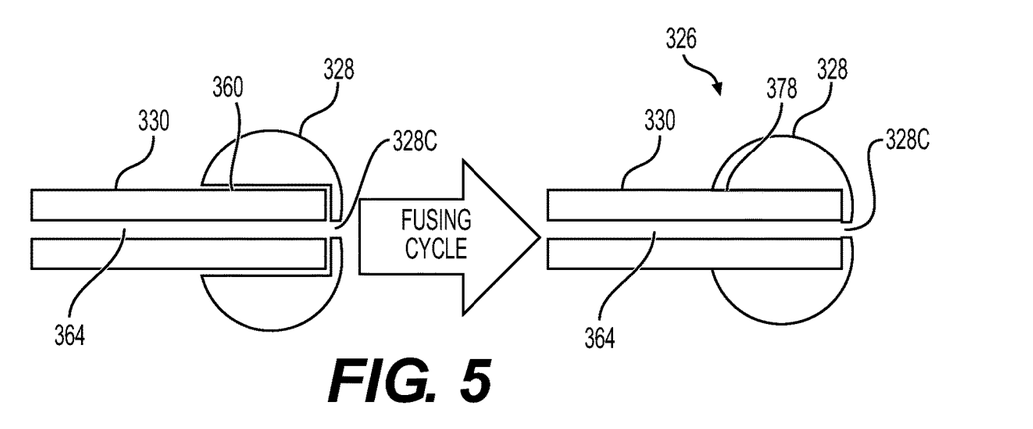
FIG. 5 illustrates views of a portion of another alternative exemplary electrode of the medical device of FIGS. 1A and 1B in stages of formation, according to aspects of the disclosure.

FIG. 5 illustrates steps of an exemplary method that may be performed to form an electrode 326 similar to electrode 26, with similar elements shown by 300 added to the reference numbers. For example, electrode 326 includes an insulation tip 328 on an electrode shaft 330. Insulation tip 328 may be a preformed element formed of an insulating material, for example, a glass (e.g., a silicate, a borosilicate, or any biocompatible glass) discussed herein, and electrode shaft 330 may be metallic (e.g., stainless steel). Insulation tip 328 may be positioned around a distal tip 360 of electrode shaft 330. As shown, insulation tip 328 may include an insulation tip lumen 328C, which may be at least partially aligned with an electrode shaft lumen 364. Then, insulation tip 328 and electrode shaft 330 may be subjected to a fusing cycle. For example, the fusing cycle may include one or more sequences or rounds of heating and cooling to soften insulation tip 328 (e.g., formed of a glass). The fusing cycle may at least partially melt insulation tip 328 such that a portion of insulation tip 328 fuses or bonds to a portion of electrode shaft 330, for example, to form an interface 378. Interface 378 may be formed on a radially outer portion of the distal portion of electrode shaft 330, and may also be formed on a distal end portion of electrode shaft 330.

Although not shown, electrode shaft 330 may include one or more surface contours, which may help secure insulation tip 328 to electrode shaft 330. Furthermore, one or more molds or other compression elements may be positioned around insulation tip 328 during the fusing cycle, for example, to help shape insulation tip 328 and/or couple insulation tip 328 to electrode shaft 330. Additionally, although not shown, one or more additional processes may be performed to smooth, shape, or otherwise treat insulation tip 328. Moreover, multiple insulation tips 328 may be placed on multiple portions of electrode shaft 330, for example, longitudinally spaced along different portions of electrode shaft 330.

Figure 6:
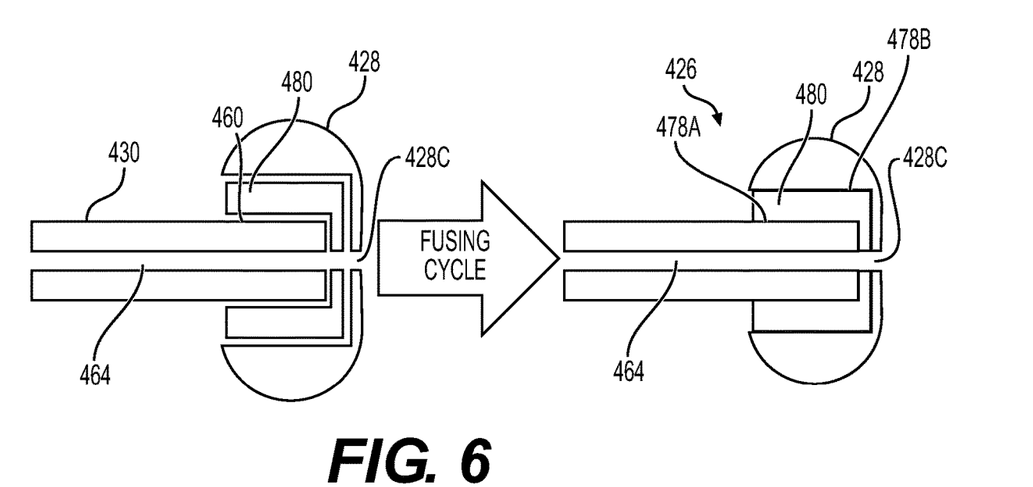
FIG. 6 illustrates views of a portion of a further alternative exemplary electrode of the medical device of FIGS. 1A and 1B in stages of formation, according to aspects of the disclosure.

FIG. 6 illustrates steps of an exemplary method that may be performed to form an electrode 426 similar to electrode 26, with similar elements shown by 400 added to the reference numbers. For example, electrode 426 includes an insulation tip 428 on an electrode shaft 430. Insulation tip 428 may be a preformed bead or other element formed of a ceramic or other insulating or non-conductive material discussed herein, and electrode shaft 430 may be metallic (e.g., stainless steel). Additionally, a coupling element 480 may be positioned between insulation tip 428 and electrode shaft 430. Insulation tip 428 and coupling element 480 may be positioned around a distal tip 460 of electrode shaft 430. As shown, insulation tip 428 may include an insulation tip lumen 428C, which may be at least partially aligned with an electrode shaft lumen 464. Coupling element 480 may also include a central lumen to allow for fluid to flow from electrode lumen 464 to insulation tip lumen 428C.

Coupling element 480 may be formed of a glass bead (e.g., a silicate, a borosilicate, or any biocompatible glass), a ceramic bead, a metal bead, or similar appropriate material. Once insulation tip 428 and coupling element are positioned on electrode shaft 430, insulation tip 428, electrode shaft 430, and coupling element 480 may be subjected to a fusing cycle. For example, the fusing cycle may include one or more sequences or rounds of heating and cooling. The fusing cycle may at least partially melt coupling element 480 such that a portion of coupling element 480 fuses or bonds to a portion of electrode shaft 430, for example, to form a first interface 478A. Moreover, the fusing cycle may at least partially melt another portion of coupling element 480 such that the other portion of coupling element 480 fuses or bonds to a portion of insulation tip 428, for example, to form a second interface 478B. In this aspect, coupling element 480 may help couple insulation tip 428 to electrode shaft 430.

First interface 478A may be formed on a radially outer portion of the distal portion of electrode shaft 430, and may also be formed on a distal end portion of electrode shaft 430. Second interface 478B may be formed on a radially outer portion of coupling element 480, and may also be formed on a distal end portion of coupling element 480.

As mentioned above, one or more of electrode shaft 440 and coupling element 480 may include one or more surface contours, which may help secure coupling element 480 to electrode shaft 440 and/or insulation tip 428 to coupling element 480, e.g., to promote formation of first interface 478A and/or second interface 478B. Furthermore, one or more molds or other compression elements may be positioned around insulation tip 428 and coupling element 480 during the fusing cycle, for example, to help shape insulation tip 428 and/or couple insulation tip 428, coupling element 480, and electrode shaft 430. Additionally, although not shown, one or more additional processes may be performed to smooth, shape, or otherwise treat insulation tip 428. Moreover, multiple insulation tips 428 and coupling elements 480 may be placed on multiple portions of electrode shaft 430, for example, longitudinally spaced along different portions of electrode shaft 430. Furthermore, if insulation tip 428 is formed of a ceramic material, a radially inner face (e.g., the portion that abuts coupling element 480 at second interface 478B) may be treated (e.g., via a sintering process, a physical vapor deposition process, etc.) to metallize a portion of insulation tip 428. Treating the portion of insulation tip 428 may help to improve the strength of the bond between insulation tip 428 and coupling element 480 at second interface 478B.

Figure 7:
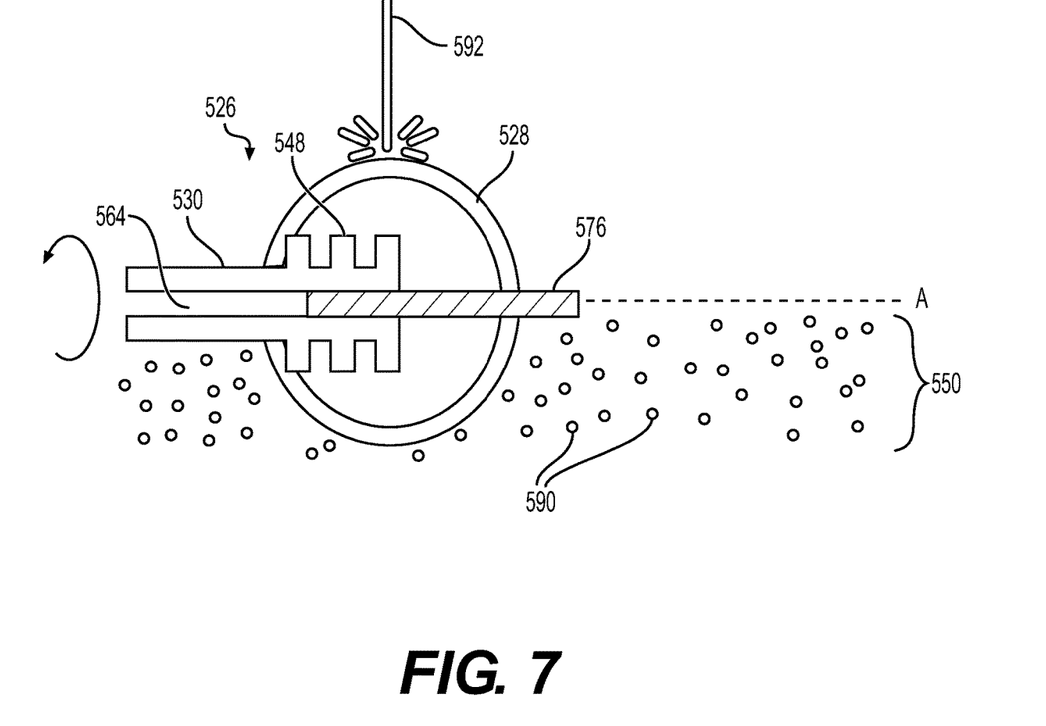
FIG. 7 illustrates a view of another alternative exemplary electrode of the medical device of FIGS. 1A and 1B during a formation process, according to aspects of the disclosure.

FIG. 7 illustrates a step of an exemplary method that may be performed to form an electrode 526 similar to electrode 26, with similar elements shown by 500 added to the reference numbers. For example, electrode 526 includes an insulation tip 528 on an electrode shaft 530. Electrode shaft 530 may include one or more surface contours 548 and an electrode shaft lumen 564. A sacrificial element 576 may be positioned within a portion of electrode shaft lumen 564, for example, to form an insulation tip lumen (not shown). Alternatively, electrode shaft lumen 564 may be open, and insulating material 550 may cover electrode shaft lumen 564, for example, for treatments that do not require fluid delivery.

Electrode shaft 530 may be positioned adjacent to (i.e., in abutting contact) with a supply of insulating material 550. In one aspect, insulating material 550 includes a plurality of insulating particles 590 (e.g., a powder or beads). Additionally, as discussed below, insulating material 550 may include one or more filler materials. A heating element 592, for example, a laser (e.g., a thermal laser, a carbon dioxide laser, a pulse diode laser, etc.) may be directed toward the supply of insulating material 550. Alternatively or additionally, heating element 592 may be directed toward a portion of electrode shaft 530. In either aspect, electrode shaft 530 may be rotated around a longitudinal axis A while heating element 592 is activated. As shown, longitudinal axis A is perpendicular to the direction of the output of heating element 592. Alternatively, electrode shaft 530 may be positioned at other angles relative to heating element 592 and/or relative to the supply of insulating material 550.

A distal portion of electrode shaft 530, for example, surface contours 548, may contact molten insulating particles 590 in the supply of insulating material 550, and insulating particles 590 may be entrained or otherwise bonded to electrode shaft 530. Energy from heating element 592 may be directed toward the supply of insulating material 550, and electrode shaft 530 may be rotated to contact molten insulating particles until a desired amount of insulating material is coupled to electrode shaft 530 to form insulation tip 528. Although not shown, additionally processing steps may be performed on insulation tip 528, for example, to cool, smooth, shape, or otherwise treat insulation tip 528. For example, as discussed above, a mold may be used and/or sacrificial element 576 may be removed to form an insulation tip lumen, and a portion of insulation tip 528 may be heated to smooth the distal end of the formed insulation tip lumen.

Figure 8A:
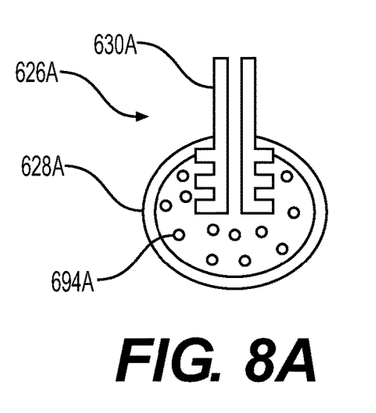
FIGS. 8A and 8B illustrate views of yet another alternative exemplary electrode of the medical device of FIGS. 1A and 1B, according to aspects of the disclosure.
Figure 8B:
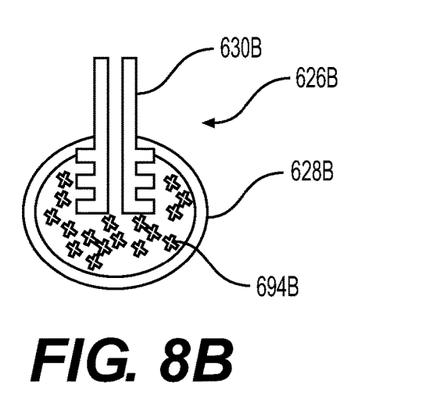

FIGS. 8A and 8B illustrate additional electrodes 626A and 626B, which are similar to electrode 26, with similar elements shown by 600 added to the reference numbers. For example, electrode 626A includes an insulation tip 628A on an electrode shaft 630A, and electrode 626B includes an insulation tip 628B on an electrode shaft 630B. Insulation tips 628A and 628B may be coupled to electrode shafts 630A and 630B via any of the techniques discussed herein. Moreover, as shown, electrodes 626A and 626B include respective filler materials 694A and 694B. For example, insulation tips 628A and 628B may be doped with one or more filler materials 694A or 694B. Filler material 694A may include a powder mixed with the material forming insulation tip 628A, and filler material 694B may include fibers or meshes mixed with the material forming insulation tip 628B.

Filler materials 694A and 694B may help to match an impedance thermal expansion of insulation tips 628A and 628B to an impedance of electrode shafts 630A and 630B, respectively. For example, as discussed above, insulation tips 628A and 628B and electrode shafts 630A and 630B are formed of different materials, which may have different rates of thermal expansion or contraction when heated (e.g., during energy delivery) or cooled. In this aspect, filler materials 694A and 694B may help to adjust a thermal expansion or contraction of insulation tips 628A and 628B to be closer to a thermal expansion or contraction of electrode shafts 630A and 630B, which may help to reduce the risk of separation and/or breakage of insulation tips 628A and 628B from electrode shafts 630A and 630B during the delivery of energy through electrodes 626A and 626B. For example, filler materials 694A and 694B may have thermal expansion coefficients between a thermal expansion coefficient of the material forming insulation tips 628A and 628B (e.g., glass, ceramic, etc.) and a thermal expansion coefficient of the material forming electrode shafts 630A and 630B (e.g., stainless steel).

Filler materials 694A and 694B may be non-conductive or have low conductivity, which at low doping levels does not provide an electrical pathway through the insulating material forming insulation tips 628A and 628B. For example, filler materials 694A and 694B may be formed of tantalum, tungsten, tungsten oxide, platinum, palladium, iridium, gold, etc. Additionally, in some aspects, filler materials 694A and 694B may be radiopaque, which may help a user visualize insulation tips 628A and 628B during a treatment procedure (e.g., via medical imaging, such as an X-ray, an MRI, ultrasound, etc.). Furthermore, filler materials 694A and 694B may be incorporated in any of the aspects discussed herein, for example, within the insulating material 150 deposited on an electrode shaft, interspersed within the insulating material 550 entrained on a portion of an electrode shaft, etc.

The various electrodes discussed herein are capable of modifying physical properties of tissue when in contact with tissue by delivering energy (e.g., radio frequency energy). The energy delivered may be monopolar or bipolar energy. The various electrodes may be coupled to a shaft, with the shaft configured to extend into a body lumen or cavity of a subject. The shaft includes an electrical element traversing the shaft and connecting the electrode to an energy source, for example, in the handle or coupled to the handle.

As discussed, the electrodes may also be coupled to an actuation member (e.g., movable body 20), for example, in the handle or coupled to the handle, that allows a user to translate the electrode relative to the shaft. The electrode may be translatable between at least a first position in which a cutting shaft (e.g., longitudinal portion 62), of the electrode is retracted within the shaft, and a second position in which the cutting shaft is extended beyond the shaft and exposed. In both the first and second positions, the distal portion that includes the insulated portions (e.g., insulation tip 28 or tips with insulating layers forming the exterior layer of the tips) may be extended and exposed beyond the shaft, and not retracted within the shaft. Moreover, the handle may allow for the electrodes to be positioned in one or more intermediate position (i.e., a position in which only a portion of longitudinal portion 62 is exposed).

As such, the insulated distal end face (e.g., insulation tip 28 or tips with insulating layers forming the exterior layer of the tips) may abut tissue and help to prevent or minimize damage or unintended contact of the electrode with the tissue. The user may also position the uninsulated electrode shaft to abut or contact tissue and apply energy to cut, dissect, ablate, mark, or otherwise treat tissue. The insulation tips may be coupled to the electrode shaft in various ways, which may allow for the insulation tip to be coupled to an existing uninsulated electrode shaft and then used in a procedure.

In one example, an electrosurgical generator coupled to the handle (or within the handle) may generate energy in various modes, for example, radio frequency energy in a cutting mode, a coagulation mode, etc., in order for the electrode to deliver these different modes of energy to the tissue. In one aspect, the electrosurgical generator and/or the handle may include one or more knobs, dials, buttons, etc. in order to select the energy mode. Additionally, in one example, a fluid source (e.g., a saline source) coupled to the handle may provide fluid (e.g., saline) to be delivered through the electrode to the tissue and/or the target site. The fluid may be delivered at a constant rate, a pulsed rate, a user-controlled rate, etc. In these aspects, one or more of the energy delivery and/or the fluid delivery may be controlled by one or more actuators (e.g., triggers, buttons, touch screens, foot pedals, etc.).

Some of the medical devices and methods discussed above allow a user to treat tissue by delivering electrical energy into the tissue, and delivering fluid, either simultaneously or sequentially. For example, a user may couple an electrode to the distal end and deliver the distal end to an interior lumen of a subject to deliver medical therapy in a portion of a procedure (e.g., mark, cauterize, or resect tissue). The insulation tip (or insulating layer forming the exterior of a tip) may help to prevent or reduce damage and/or unintended contact between the electrode and the tissue. The user may also deliver fluid distally out of the distal end of the electrode, either simultaneously or sequentially with the energy delivered, which may help the user to more quickly and efficiently deliver the medical therapy, for example, cut, dissect, ablate, mark, coagulate, cauterize, or otherwise treat tissue. Moreover, the user may deliver fluid and energy without removing the medical device from the patient or subject, which may help to reduce the costs and duration of the procedure, also potentially reducing the risks to the subject.

Additionally, various aspects of the disclosure may allow for insulation tip 28 to be formed and coupled to a distal portion of electrode shaft 30. For example, aspects discussed herein may help provide a strong coupling between the conductive material of electrode shaft 30 and the non-conductive material of insulation tip 28. Moreover, the formation of insulation tip 28 and the coupling of insulation tip 28 to electrode shaft 30 may be labor and/or cost-effective. Furthermore, in some aspects, the methods of forming and coupling insulation tip 28 to electrode shaft 30 may help to form insulation tip lumen 28C, for example, such that fluid may be delivered through electrode shaft lumen 64 and through insulation tip lumen 28C.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A method of forming an energy delivery portion of a medical device, the method comprising:
    contacting a distal portion of an electrode shaft with an insulating material; and
    heating the insulating material to couple the insulating material to the distal portion of the electrode shaft to form an insulation tip,
    wherein the distal portion of the electrode shaft includes one or more surface contours to entrain the insulating material, and
    wherein the electrode shaft includes stainless steel, and wherein the insulating material includes a glass or a ceramic.

2. The method of claim 1, further comprising shaping the insulating material in a mold such that the insulation tip insulates a distal end face of the electrode shaft.

3. The method of claim 2, wherein the electrode shaft includes an electrode shaft lumen, and further comprising an initial step of inserting a sacrificial element into a portion of the electrode shaft lumen.

4. The method of claim 3, further comprising removing the sacrificial element after the heating of the insulating material and shaping of the insulating material in the mold to form an insulation tip lumen that at least partially aligns with the electrode shaft lumen.

5. The method of claim 1, wherein the heating of the insulating material precedes the contacting the distal portion of the electrode shaft with the insulating material.

6. The method of claim 1, wherein the contacting the distal portion of the electrode shaft with the insulating material includes depositing the insulating material from a molten bath on the distal portion of the electrode shaft.

7. The method of claim 1, wherein the contacting the distal portion of the electrode shaft with the insulating material includes positioning a glass bead around the distal portion of the electrode shaft and positioning a non-conductive material around the glass bead, and further comprising fusing the non-conductive material to the electrode shaft by at least partially melting the glass bead.

8. The method of claim 1, wherein the contacting the distal portion of the electrode shaft with the insulating material includes positioning the electrode shaft adjacent to a supply of insulating material, and rotating the electrode shaft, and wherein the heating the insulating material includes directing energy from a laser toward the electrode shaft or the insulating material.

9. The method of claim 1, further comprising cooling the insulating material and the electrode shaft at a controlled rate for approximately one hour.

10. The method of claim 1, wherein the surface contours include a plurality of circumferential projections or a roughened surface.

11. The method of claim 10, wherein the surface contours are formed by machining.

12. The method of claim 1, wherein the insulating material further includes one or more filler materials.

13. The method of claim 12, wherein the one or more filler materials have a thermal expansion coefficient between a thermal expansion coefficient of the glass or the ceramic and a thermal expansion coefficient of a material forming the electrode shaft.

14. A method of forming an energy delivery portion of a medical device, the method comprising:

positioning a coupling element around a distal portion of an electrode shaft;

positioning a bead of insulating material around the coupling element; and heating the coupling element to at least partially melt the coupling element to secure the bead of insulating material to the electrode shaft.

15. The method of claim 14, further comprising compressing the bead of insulating material around the heated coupling element.

16. The method of claim 14, wherein the coupling element is formed of glass and the bead of insulating material is formed of ceramic, and wherein the method further comprises an initial step of sintering or depositing metallic material on an inner portion of the ceramic bead of insulating material.

17. A method of forming an energy delivery portion of a medical device, the method comprising:

positioning a sacrificial element in an electrode shaft lumen of an electrode shaft, wherein the sacrificial element extends distally beyond a distal end of the electrode shaft;

depositing an insulating material on a distal portion of the electrode shaft, wherein the insulating material is heated to an at least partially molten state;

shaping the insulating material on the distal portion of the electrode shaft to form an insulation tip on the distal portion of the electrode shaft; and removing the sacrificial element from the electrode shaft lumen and the insulating material to form an insulation tip lumen that at least partially aligns with the electrode shaft lumen.

18. The method of claim 17, wherein the insulating material is heated by directing a laser energy source toward the distal portion of the electrode shaft or toward a supply of the insulating material.

19. The method of claim 18, wherein the insulating material is deposited on the distal portion of the electrode shaft by positioning the electrode shaft adjacent to the supply of insulating material, and rotating the electrode shaft.

* * * * *